(12) United States Patent
Agahi et al.

(10) Patent No.: US 12,263,122 B2
(45) Date of Patent: *Apr. 1, 2025

(54) METHODS OF SOLENOID VALVE CONTROL OPTIMIZATION

(71) Applicant: Alcon Inc., Fribourg (CH)

(72) Inventors: Daryush Agahi, Irvine, CA (US); Jiansheng Zhou, Cerritos, CA (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/181,267

(22) Filed: Mar. 9, 2023

(65) Prior Publication Data

US 2023/0201033 A1      Jun. 29, 2023

Related U.S. Application Data

(63) Continuation of application No. 16/661,157, filed on Oct. 23, 2019, now Pat. No. 11,642,243.

(60) Provisional application No. 62/777,406, filed on Dec. 10, 2018.

(51) Int. Cl.
| | |
|---|---|
| F16K 31/06 | (2006.01) |
| A61F 9/007 | (2006.01) |
| F16K 37/00 | (2006.01) |
| G05D 7/06 | (2006.01) |
| H01F 7/06 | (2006.01) |
| H01F 7/16 | (2006.01) |
| A61B 17/00 | (2006.01) |

(52) U.S. Cl.
CPC ...... *A61F 9/00763* (2013.01); *F16K 31/0603* (2013.01); *F16K 37/0041* (2013.01); *G05D 7/0623* (2013.01); *G05D 7/0635* (2013.01); *H01F 7/064* (2013.01); *H01F 7/16* (2013.01); *A61B 2017/0019* (2013.01); *A61B 2017/00544* (2013.01)

(58) Field of Classification Search
CPC ............ F16K 31/0603; F16K 37/0041; A61F 9/00763; A61F 9/00736; G05D 7/0623; G05D 7/0635; H01F 7/064; H01F 7/16; A61B 2017/00544; A61B 2017/0019
See application file for complete search history.

(56) References Cited

U.S. PATENT DOCUMENTS

| | | | | |
|---|---|---|---|---|
| 4,006,386 A | * | 2/1977 | Duggan | ................ H01F 7/1844 |
| | | | | 361/240 |
| 4,321,946 A | * | 3/1982 | Paulos | ................ F16K 37/0041 |
| | | | | 166/66.4 |
| 2002/0049461 A1 | | 4/2002 | Kanda et al. | |
| 2010/0145374 A1 | | 6/2010 | Perkins et al. | |

FOREIGN PATENT DOCUMENTS

| | | |
|---|---|---|
| JP | 2002-181220 A | 6/2002 |
| JP | 2011-179647 A | 9/2011 |
| JP | 2015-500689 A | 1/2015 |
| WO | 98/08442 A1 | 3/1998 |

* cited by examiner

*Primary Examiner* — Matthew W Jellett
(74) *Attorney, Agent, or Firm* — PATTERSON + SHERIDAN, LLP

(57) ABSTRACT

Systems and methods for optimizing the application of pulse width modulation (PWM) in a voltage signal for delivering a current in a valve used to alternatively deliver pressurized gas to and vent from chambers in a vitrectomy probe used to drive a cutter.

11 Claims, 15 Drawing Sheets

METHODS OF SOLENOID VALVE CONTROL OPTIMIZATION

CROSS-REFERENCE TO RELATED APPLICATIONS

This application is a continuation of U.S. Non-Provisional patent application Ser. No. 16/661,157, filed Oct. 23, 2019, which claims the benefit of priority of U.S. Provisional Patent Application Ser. No. 62/777,406 titled "Methods of Solenoid Valve Control Optimization", filed on Dec. 10, 2018, whose inventors are Daryush Agahi and Jiansheng Zhou, which is hereby incorporated by reference in its entirety as though fully and completely set forth herein.

BACKGROUND

Field of the Disclosure

The present disclosure relates to optimizing the application of pulse width modulation (PWM) in a voltage signal for delivering a current in a valve for driving a vitrectomy probe.

Description of Related Art

Vitreo-retinal procedures may include a variety of surgical procedures performed to restore, preserve, and enhance vision. Vitreo-retinal procedures may be appropriate to treat many serious conditions of the back of the eye. Vitreo-retinal procedures may treat conditions such as age-related macular degeneration (AMD), diabetic retinopathy and diabetic vitreous hemorrhage, macular hole, retinal detachment, epiretinal membrane, CMV retinitis, and many other ophthalmic conditions.

The vitreous is a normally clear, gel-like substance that fills the center of the eye. It may make up approximately % of the eye's volume, giving it form and shape before birth. Certain problems affecting the back of the eye may require a vitrectomy, or surgical removal of the vitreous. Removal of vitreous can involve a vitrector, or cutting device, that works like a tiny guillotine, with an oscillating microscopic cutter to remove the vitreous gel in a controlled fashion. Operating the cutter at a high cut rate may prevent significant traction on the retina during the removal of the vitreous humor. Also, the cutter can be driven by a pneumatic module that may condition and supply compressed air or gas to power the cutter.

SUMMARY

The disclosed embodiments of the present technology relate to optimizing the application of pulse width modulation (PWM) in a voltage signal for delivering a current in a valve used to alternatively deliver pressurized gas to and vent from chambers in a vitrectomy probe used to drive a cutter.

Some embodiments of the present technology involve a system for solenoid valve control optimization for a vitrectomy probe that includes a vitrectomy probe with a first chamber and a second chamber on respective sides of a pneumatically driven diaphragm for reciprocating a probe cutter. The system also includes a valve coupled with a pressurized gas source. The valve can include a solenoid which, when supplied with a current, moves a solenoid plunger of the valve to alternatively deliver and vent pressurized gas through a first outlet line and a second outlet line which respectively deliver and vent pressurized gas to and from the first chamber and to and from the second chamber of the vitrectomy probe.

The system can also include a power supply for supplying a voltage to drive a current in the solenoid and a current sensor coupled to the solenoid and configured to monitor current in the solenoid and transmit a current signal. A system controller can be communicatively coupled with the power supply and the current sensor and the system controller can receive the current signal from the current sensor and identify when a movement of the solenoid plunger creates a back electromotive force (back EMF) that changes the current in the solenoid in a predetermined degree. After detecting the back EMF indicating the solenoid plunger is moving or finished moving, the system controller can enter a pulse width modulation (PWM) mode of operation with reduced power consumption to keep it moving and or hold the end position of solenoid plunger until power to the solenoid is turned off at a predetermined timing.

In some cases, the system controller observes that the current is higher in each of a series of samples at the sampling rate, observes that a subsequent series of subsequent samples in a sampling band are successively lower and resulted in a total current drop greater than a predetermined threshold, observes that another series of subsequent samples are successively higher indicating a rebound in the current after the current rebounded from a valley, and identifies a movement of the solenoid plunger created back EMF by observing the valley.

In some cases, the controller observes that the current is higher in each of a series of samples at the sampling rate, observes that a subsequent series of subsequent samples in a sampling band are successively lower and resulted in a total current drop greater than a predetermined threshold indicating a peak, and identifies a movement of the solenoid plunger created back EMF by observing the peak.

In some cases, the system controller identifies a peak and/or valley when the current drop reaches predetermined current drop of 10 milliamps. The system controller can also apply various PWM modes including a constant PWM with a fixed duty cycle and a fixed frequency and a variable PWM with a variable duty cycle and a variable frequency. In some cases, the valve, the power supply, the current sensor, and the system controller are integrated in an ophthalmic surgical console.

Some embodiments of the present technology involve a method of optimizing control of a solenoid valve for operating a vitrectomy probe. The method of optimizing control of a solenoid valve for operating a vitrectomy probe can involve coupling a valve with a pressurized gas source, a power supply for supplying a voltage to drive a current in a solenoid in the valve, and a vitrectomy probe with a first chamber and a second chamber on respective sides of a pneumatically driven diaphragm for reciprocating a probe cutter. The method can also include delivering, by the power supply, a voltage to supply the solenoid with a current which drives a solenoid plunger of the valve to alternatively deliver and vent pressurized gas through a first outlet line and a second outlet line which respectively deliver and vent pressurized gas to and from the first chamber and to and from the second chamber of the vitrectomy probe.

Next, the method can include monitoring, with a current sensor coupled to the solenoid, the current in the solenoid, transmitting, by the current sensor to a system controller, a current signal, and receiving, by the system controller, the current signal from the current sensor. After receiving the current signal, the method can involve identifying, by the system controller, when a movement of the solenoid plunger creates a back electromotive force (back EMF) that changes the current in the solenoid in a predetermined degree and causing, by the system controller, the power supply to enter a pulse width modulation (PWM) mode of operation with reduced power consumption to keep the solenoid plunger moving and/or hold the end position of solenoid plunger until power to the solenoid is turned off at a predetermined timing.

In some cases, identifying when a movement of the solenoid plunger creates a back EMF involves the system controller observing that the current is higher in each of a series of samples at the sampling rate, observing that a subsequent series of subsequent samples in a sampling band are successively lower and resulted in a total current drop greater than a predetermined threshold, observing that another series of subsequent samples are successively higher indicating a rebound in the current after the current rebounded from a valley, and identifying a movement of the solenoid plunger created back EMF by observing the valley.

In some cases, identifying when a movement of the solenoid plunger creates a back EMF involves the system controller observing that the current is higher in each of a series of samples at the sampling rate, observing that a subsequent series of subsequent samples in a sampling band are successively lower and resulted in a total current drop greater than a predetermined threshold indicating a peak, and identifying a movement of the solenoid plunger created back EMF by observing the peak.

In some cases, the system controller identifies a peak and/or valley when the current drop reaches a predetermined current drop of 10 milliamps. The system controller can also apply various PWM modes including a constant PWM with a fixed duty cycle and a fixed frequency and a variable PWM with a variable duty cycle and a variable frequency. In some cases, the valve, the power supply, the current sensor, and the system controller are integrated in an ophthalmic surgical console.

In some cases, the method can also include collecting timing data describing a timing associated with the peaks and the valleys of the current signal, collecting a collection of quantified instances of valve failure, training, using supervised learning, a machine learning algorithm to create a prediction model for predicting future valve failures based on real-time timing data of a future valve operation, and using the failure prediction model to anticipate a future valve failure prior to a subsequent vitrectomy procedure.

In some cases, the method can also include collecting timing data describing a timing associated with the peaks and the valleys of the current signal and adjusting, based on the timing data, the valve duty cycle to compensate variations in timing of valve open or close so that the desired pressure output can be reached for actuating the vitrectomy probe.

In some cases, the method can also include collecting timing data describing a timing associated with the peaks and the valleys of the current signal, collecting a collection of quantified instances of timing variation compensation, and training, using supervised learning, a machine learning algorithm to create an adjustment model for compensating variations in timing of valve open or close based on real-time timing data of a future valve operation.

BRIEF DESCRIPTION OF THE DRAWINGS

For a more complete understanding of the present technology, its features, and its advantages, reference is made to the following description, taken in conjunction with the accompanying drawings, in which.

DESCRIPTION

The technology described below involves optimizing the application of pulse width modulation (PWM) in a voltage signal for delivering a current in a valve used to alternatively deliver pressurized gas to and vent from chambers in a vitrectomy probe used to drive a cutter.

Figure 1:
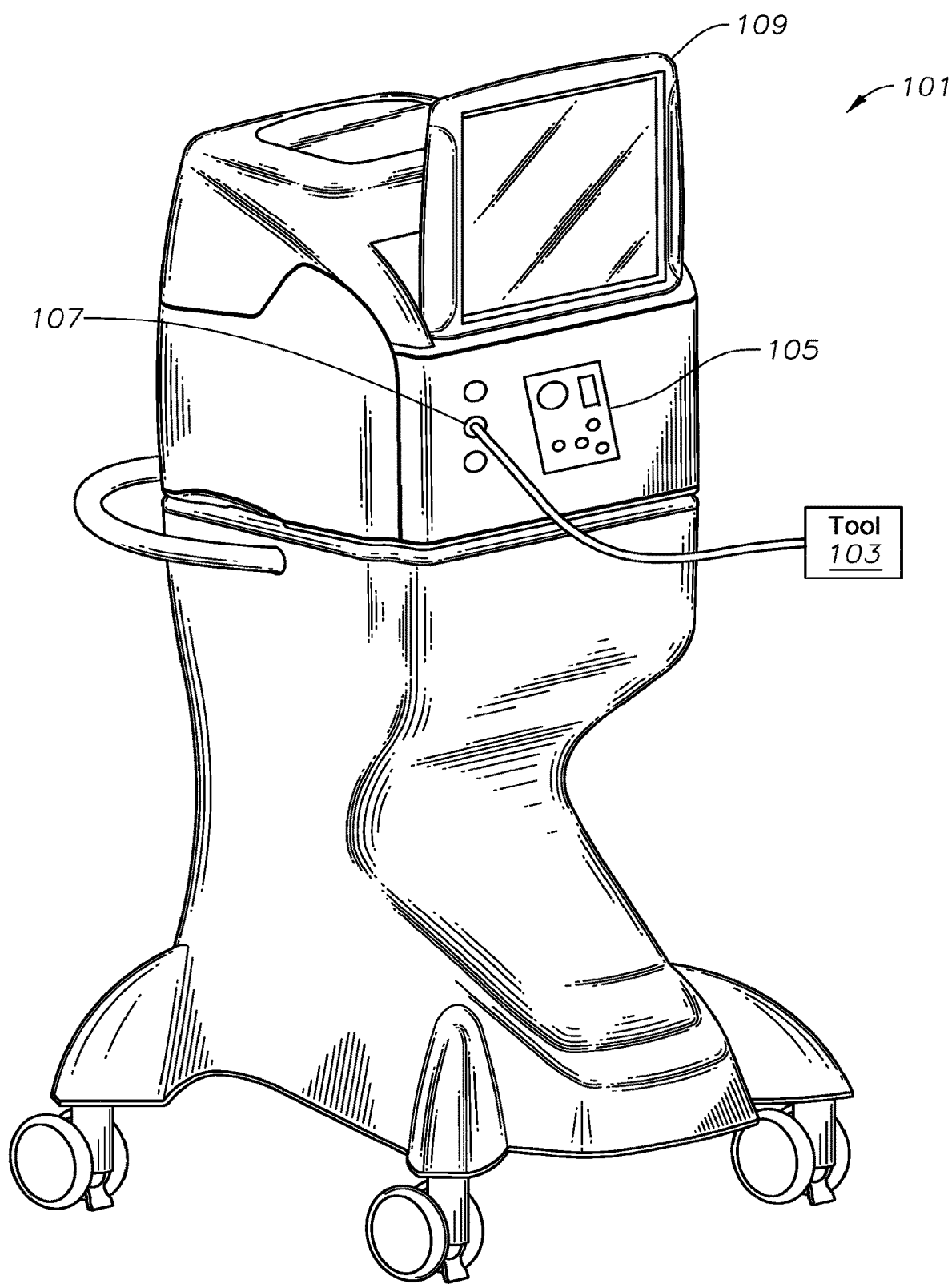
FIG. 1 illustrates an embodiment of a surgical console for a pneumatically powered ophthalmic surgical machine.

FIG. 1 illustrates an embodiment of a surgical console 101 for a pneumatically powered ophthalmic surgical machine. The surgical console 101 may be configured to drive one or more pneumatic tools 103. The tools 103 may include, for example, scissors, vitrectors, forceps, and injection or extraction modules. Other tools 103 may also be used. In operation, the pneumatically powered ophthalmic surgery machine of FIG. 1 may operate to assist a surgeon in performing various ophthalmic surgical procedures, such as a vitrectomy. A compressed gas, such as nitrogen, may provide the power through the surgical console 101 to power tools 103. The surgical console 101 may include a display 109 for displaying information to a user (the display may also incorporate a touchscreen for receiving user input). The surgical console 101 may also include a fluidics module 105 (e.g., to support irrigation/aspiration functions) and one or more port connectors 107 for coupling to tools 103 (e.g., coupling through pneumatic lines attached to the tools 103).

Figure 2A:
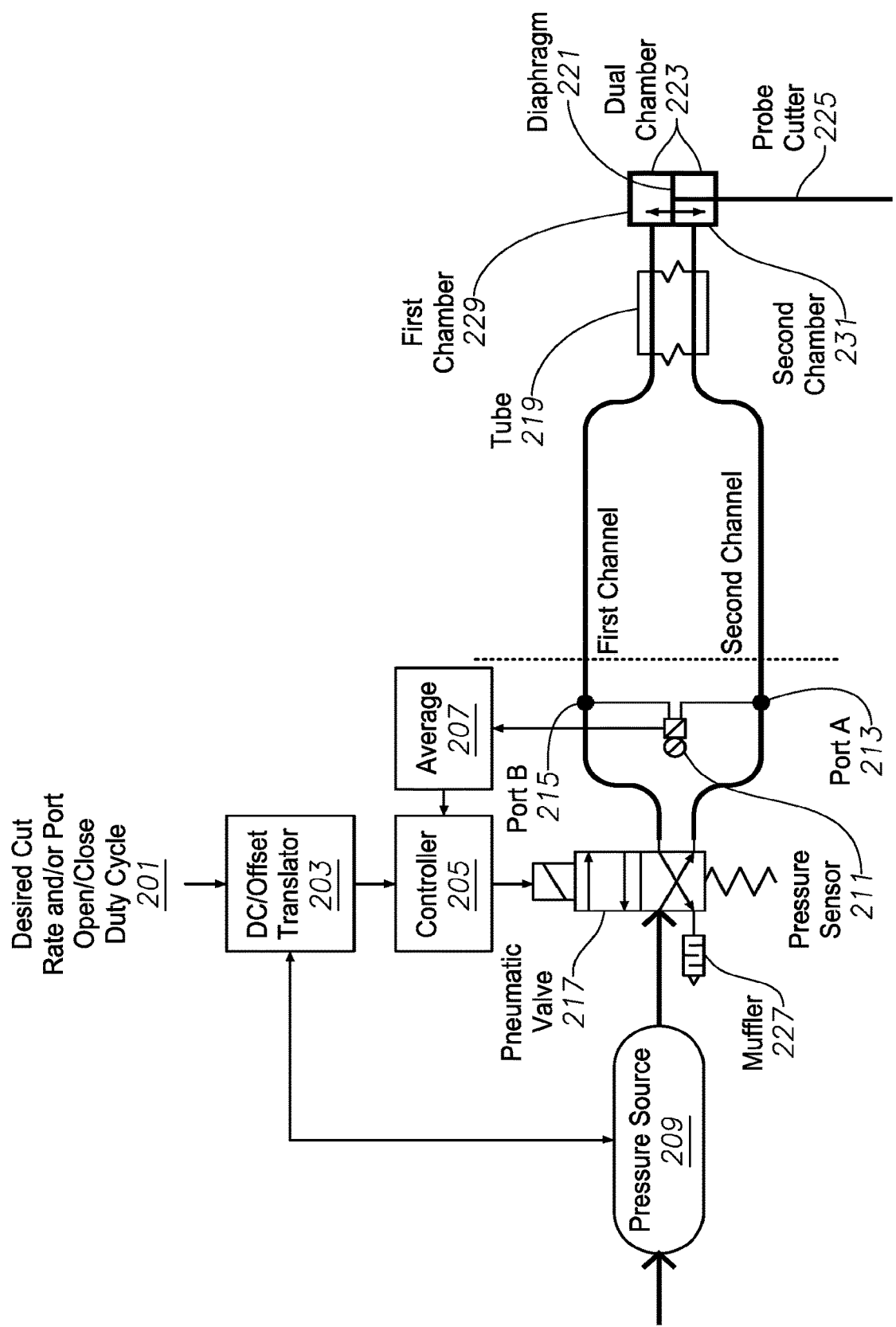
FIGS. 2a-b illustrate schematics of a pneumatic system for a pneumatically powered vitrectomy machine.
Figure 2B:
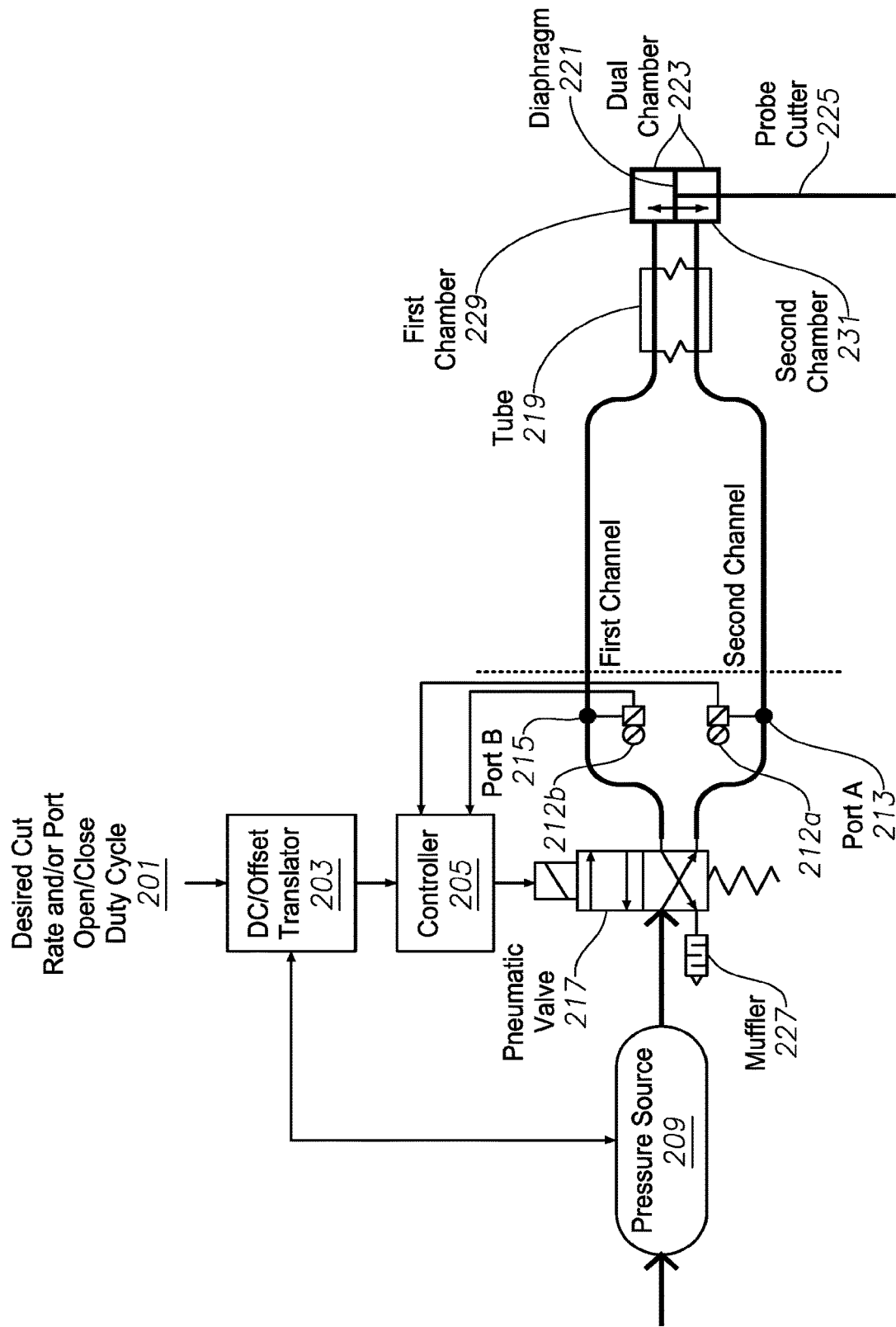

FIGS. 2A and 2B illustrate a schematic of a pneumatic system for a pneumatically powered vitrectomy machine. As seen in FIGS. 2A and 2B, the pneumatic system may include one or more pneumatic valves 217 coupling a pressure source 209 (e.g., a regulated pressure source such as an air cylinder or a wall outlet air supply) to output port A 213 and output port B 215 (the output port A 213 and output port B 215 may be coupled to the tool 103 through one or more port connectors 107). In some embodiments, the pneumatic valve 217 may be controlled by controller 205. In some embodiments, the pressure of the pressure source 209 may also be regulated by controller 205 or a separate controller (e.g., internal to the surgical console 101). The controller 205 may regulate pressure (e.g., to balance between lower pressures for reducing air consumption and higher pressures for faster cut rates and/or to increase a dynamic range of available cut rates). In some embodiments, the components of the pneumatic system may be incorporated in a manifold (e.g., machined out of a metal, such as aluminum). The manifold may be air tight, and include various fittings and couplings, and be capable of withstanding relatively high gas pressures. The manifolds may be manufactured as individual pieces or they may be manufactured as a single piece. In various embodiments, the components of the pneumatic system (e.g., in the manifold) may be incorporated inside the surgical console 101.

In some embodiments, pneumatic valve 217 may be a four-way valve. Other valve configurations are also contemplated. The valve 217 may include a solenoid that operates to move a solenoid plunger in the valve 217 to one of the two positions (e.g., see FIGS. 2a-b) as directed by control signals from controller 205. In a first position, pneumatic valve 217 may allow pressurized gas to pass through pneumatic valve 217 to output port B 215 to provide pneumatic power to the probe cutter 225 while venting pressurized gas from output port A 213 through muffler 227. In a second position, the valve 217 may provide pressurized gas to output port A 213 and vent pressurized gas from output port B 215. In this position, pressurized gas may pass through output port A 213 to provide pneumatic power to a tool 103 (e.g., probe cutter 225). Thus, when the pneumatic valve 217 is in the first position, the first chamber 229 of the dual chambers 223 may be charged while the second chamber 231 may be discharged. When the pneumatic valve 217 is in the second position the second chamber 231 may be charged while the first chamber 229 may be discharged.

Figure 3:
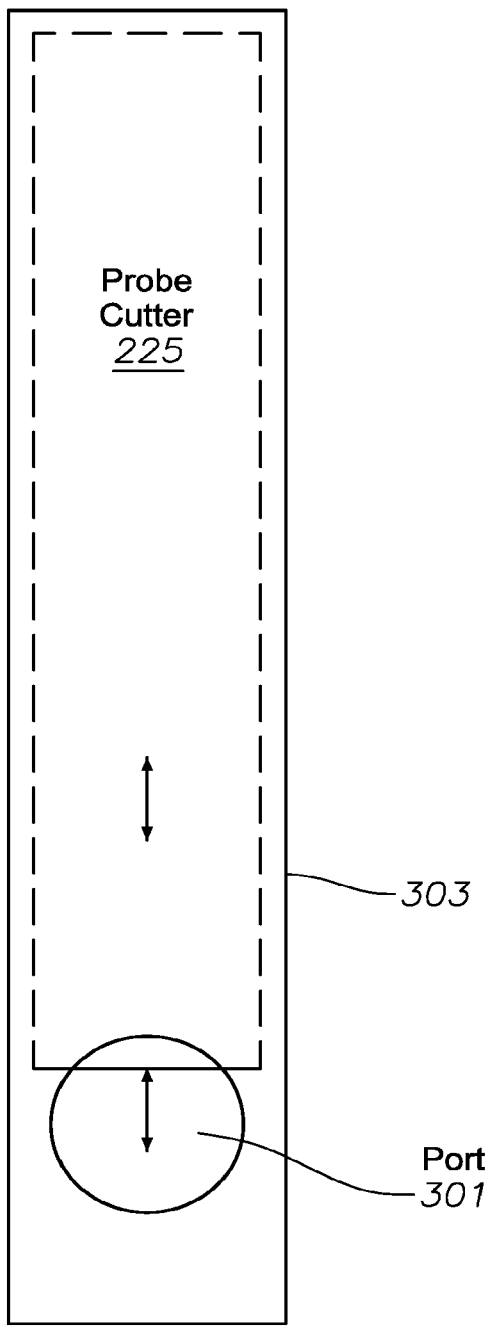
FIG. 3 illustrates a vitrectomy cutter.

As seen in FIG. 3, the probe cutter 225 may act as a cutting device. The probe cutter 225 may reciprocate inside an outer tube 303 with a cutter port 301 (e.g., the probe cutter 225 may be moved by a diaphragm 221 that in turn oscillates as pressurized gas is alternately directed to output ports A and B (and into respective chambers of the dual chamber 223)). In some embodiments, probe cutter 225 may be attached to output ports A and B through tube 219 (separate tubes for each port may also be used). As the probe cutter 225 moves back and forth, the probe cutter 225 may alternately open and close cutter port 301 with a sharpened tip of the probe cutter 225. Each cycle of the probe cutter 225 through outer tube 303 may cut through material such as vitreous in the cutter port 301 as the probe cutter 225 is closing. A port duty cycle (PDC) may indicate the amount of time the cutter port 301 is open and closed. For example, a PDC of 49% may indicate the cutter port 301 is open 49% of the cycle time (and closed 51% of the cycle time—the cycle time being, for example, the amount of time between each successive opening of the cutter port 301).

In some embodiments, the valve duty cycle (VDC) may include the amount of time the pneumatic valve 217 is in the first and second positions. In some embodiments, a cut rate of the probe cutter 225 may be controlled by the controller 205 through valve 217. For example, to provide a 2500 cuts per minute probe rate, controller 205 may direct pneumatic valve 217 to provide pressurized air alternately to port A (second channel) and port B (first channel) at a rate of approximately 24 milliseconds (ms) per cycle. To obtain a cut rate of 2500 cuts per minute, the two pneumatic channels may cycle open/closed every 24 ms (2500 cuts/min or 1 min/2500 cuts*60 seconds/1 min=0.024 seconds/cut=24 ms/cut), which may open for 12 ms to each channel.

For the benefit of reducing traction (which can cause retinal detachment) during vitrectomy procedure, the vitrectomy probe is desired to be operated at high speed. The common understanding is the faster the better. Therefore, the drive valve is often operated at its maximum speed (in CPM). At very high speed, each valve cycle time is very short, which requires the solenoid valve to move very fast in opening and closing. For example, at 15,000 cpm with 50% VDC, in each valve cycle the time duration of valve open and close is only 2 ms. Therefore the solenoid valve has to actuate very fast so that it opens and closes in less than 2 ms.

In some cases, increasing solenoid power by coil design and/or applying higher voltage along with stronger return spring can speed up the valve actuation. However, high power or high voltage can heat up the solenoid valve which can cause damage or failure. Therefore, in some cases, once the valve is actuated it enters a power saving mode through control electronics and software. In some cases, driving voltage Pulse Width Modulation can be used as a power saving mode.

Figure 4A:
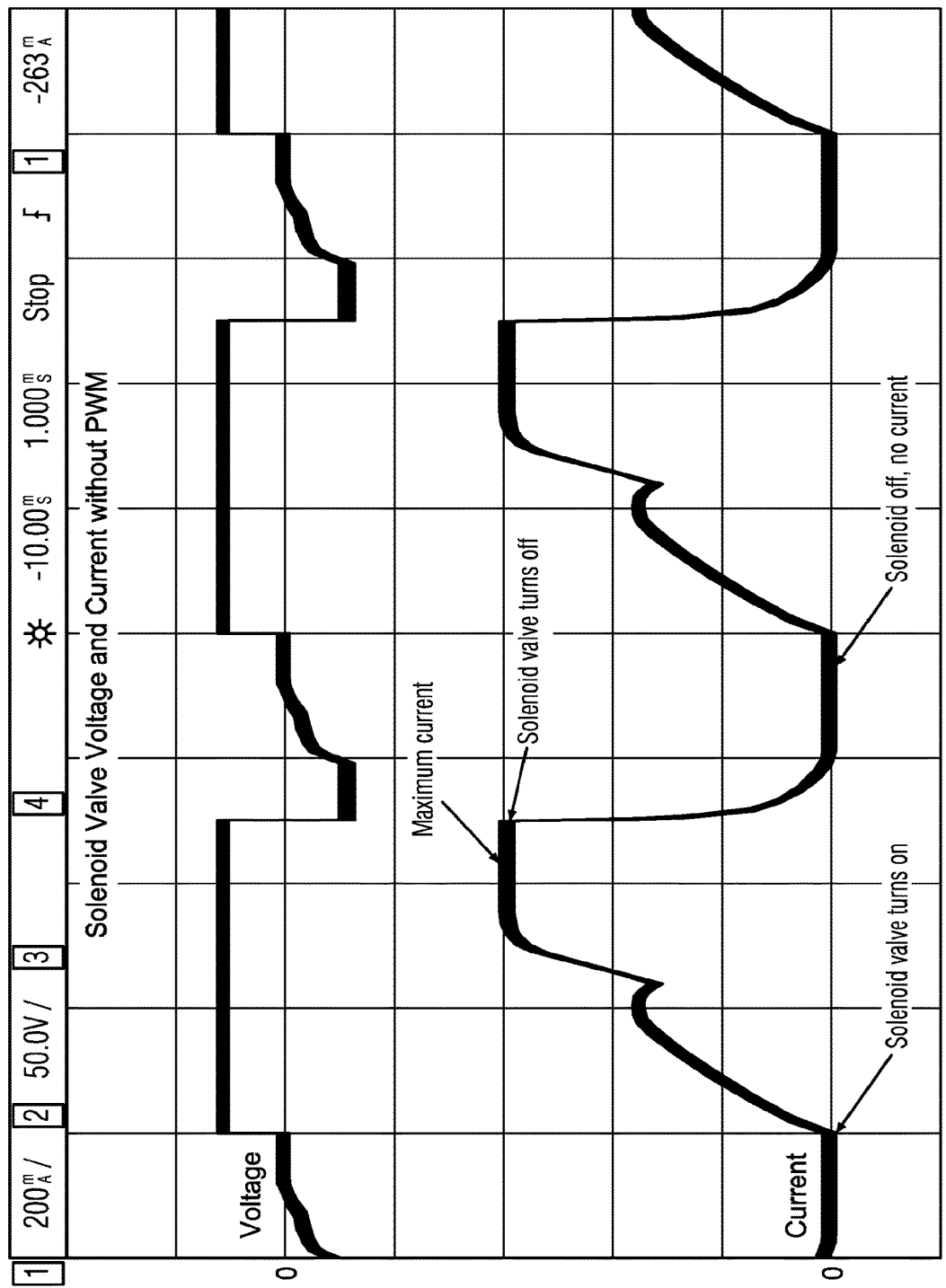
FIG. 4A illustrates prior art example plots of voltage and current over time of a solenoid vitrectomy drive valve without pulse width modulation.
Figure 4B:
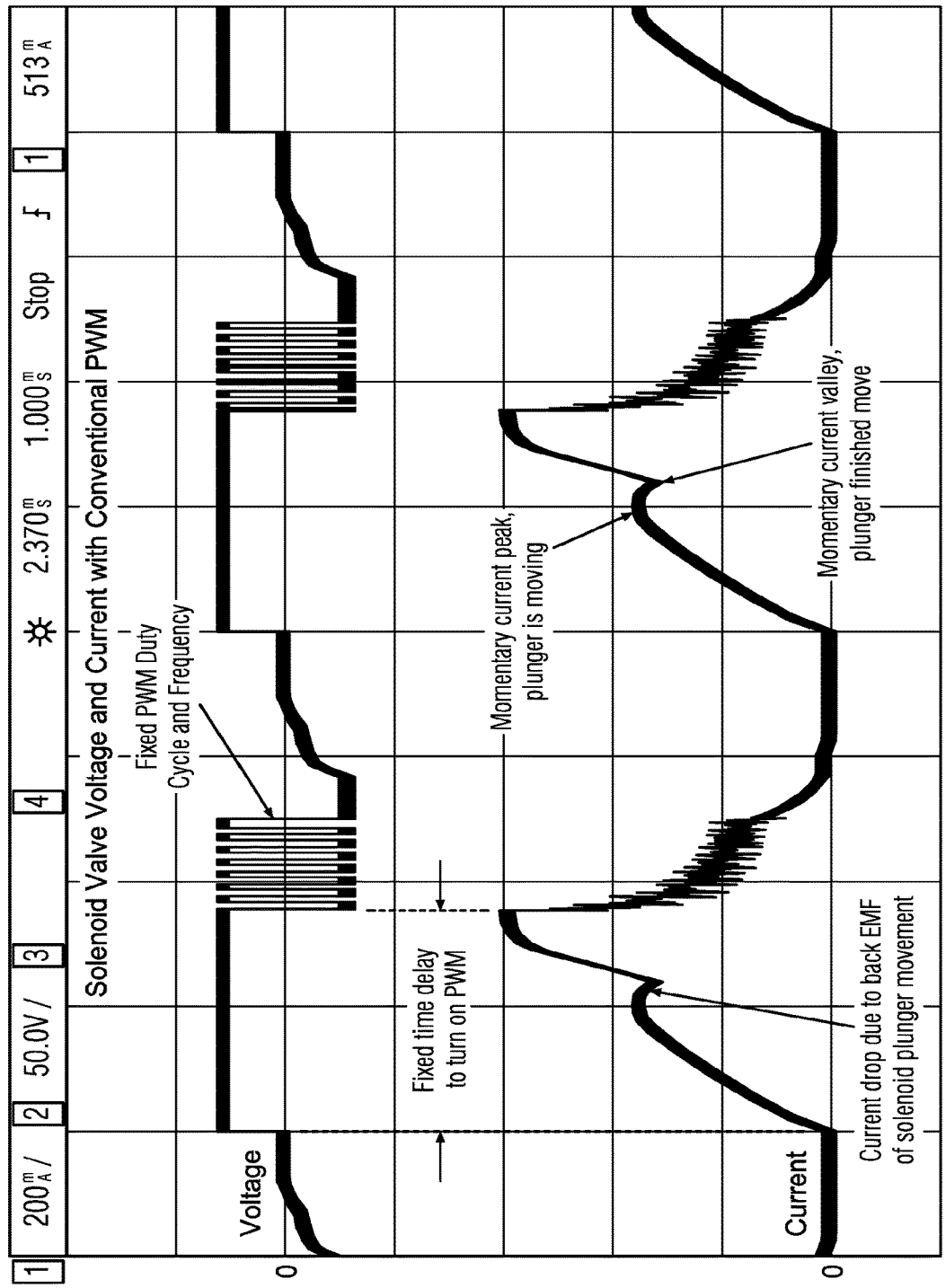
FIG. 4B illustrates prior art example plots of voltage and current over time of the same solenoid valve with pulse width modulation.

FIG. 4A illustrates prior art example plots of Voltage and Current over time of a solenoid vitrectomy drive valve operating at 15,000 cpm without PWM. FIG. 4B illustrates prior art example plots of Voltage and Current over time of the same solenoid valve with PWM. In the PWM operation shown in FIG. 4B, the average current and overall power consumption is reduced. In this case, the duty cycle and frequency of the PWM voltage signal are fixed.

In the prior art, the timing of turning on PWM could be fixed to account for a wide range of variations in the valves that can change over time. Valve to valve variations and changes of valve operation are related to temperature and the variation in timing of plunger movement. Prior art attempts to accommodate these variations have involved a fixed time delay to turn on PWM as shown in FIG. 4B. This delay has been set to be significantly longer than the time of completing plunger movement.

The present technology involves detecting when the valve solenoid plunger begins moving and, after movement begins, beginning PWM of the current to reduce mechanical impact, reduce heat, reduce noise, reduce power consumption and increase reliability and longevity.

To begin the movement of a solenoid plunger in a valve, the current is initially set at a high value to overcome inertia; however, once the solenoid plunger begins movement, less current is needed to keep the solenoid plunger moving. Also, when the solenoid valve is turned on, the solenoid plunger movement induces a back electromotive force (i.e. back EMF) in the solenoid coil, which causes momentary reduction in the solenoid current. This current change characteristic is a reliable indicator of solenoid valve movement. According to the present technology, a PWM power saving mode can start after a back EMF is detected after the solenoid plunger moves.

Figure 5:
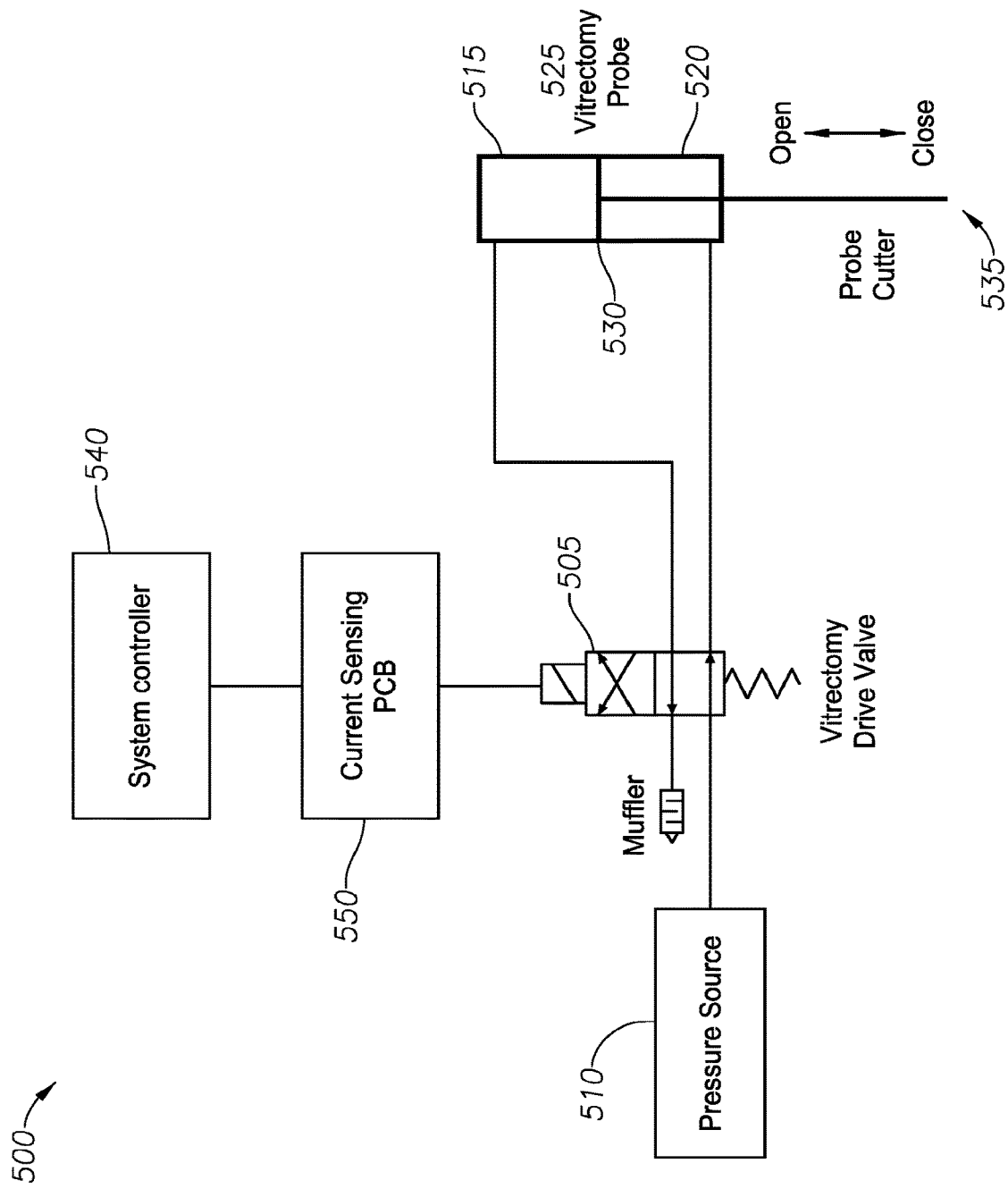
FIG. 5 illustrates a system for optimizing the application of pulse width modulation to the voltage applied to a pneumatic valve for driving a pneumatic chamber of a vitrectomy probe.

FIG. 5 illustrates a system 500 for optimizing the application of pulse width modulation to the voltage applied to a pneumatic valve for driving a pneumatic chamber of a vitrectomy probe. The system 500 includes a pneumatic valve 505 (e.g. a four-way valve) coupling a pressure source 510 (e.g., a regulated pressure source such as an air cylinder or a wall outlet air supply) to chambers 515, 520 of a vitrectomy probe 525. The valve 505 alternatively pressurizes and vents the chambers 515, 520 which drives a diaphragm 530 and reciprocates the probe cutter 535.

The pneumatic valve 505 may be controlled by a system controller 540, e.g. a controller integrated within a surgical console. The system controller 540 can include a power supply or can be coupled to a power supply. The system controller 540 can cause the power supply to deliver a voltage to the valve 505 to drive a current in a solenoid in the valve 505. The current can cause the valve to move back and forth to alternatively pressurize and vent the chambers 515, 520 of the vitrectomy probe 525. More specifically, when the pneumatic valve 505 is in the first position, the first chamber 515 is charged while the second chamber 520 is discharged. When the pneumatic valve 505 is in the second position the second chamber 520 is charged while the first chamber 515 is discharged.

The system 500 also includes a current sensor 550 that can monitor the current in the valve 505 and provide the system controller with current data. As explained above, when the solenoid plunger moves within the valve 505, the plunger induces a back electromotive force (i.e. back EMF) in the solenoid coil, which causes momentary reduction in the current. The system controller 540 can analyze the current data from the current sensor 550 and can detect changes in current caused by the back EMF indicating movement of the solenoid plunger. The system controller 540 can also execute instructions that cause the system controller 540 to begin pulse width modulation (PWM) on the voltage applied to the solenoid in the valve 505 after detecting the back EMF. In other words, the system controller 540 can actively enter a PWM mode of operation in response to the detection of back EMF instead of time-based PWM mode which results in the application PWM mode consistently more temporally close to the movement of the solenoid plunger which reduces mechanical impact, reduces heat, reduces noise, reduces power consumption and increases reliability and longevity of the valve 505.

As mentioned above, the detection of movement of a solenoid plunger in a valve can involve examining a current signal and detecting changes in the current caused by back EMF. The present technology involves various methods of detecting movement of a solenoid plunger in a valve to optimize the application of PWM on a voltage applied to the solenoid.

Figure 6A:
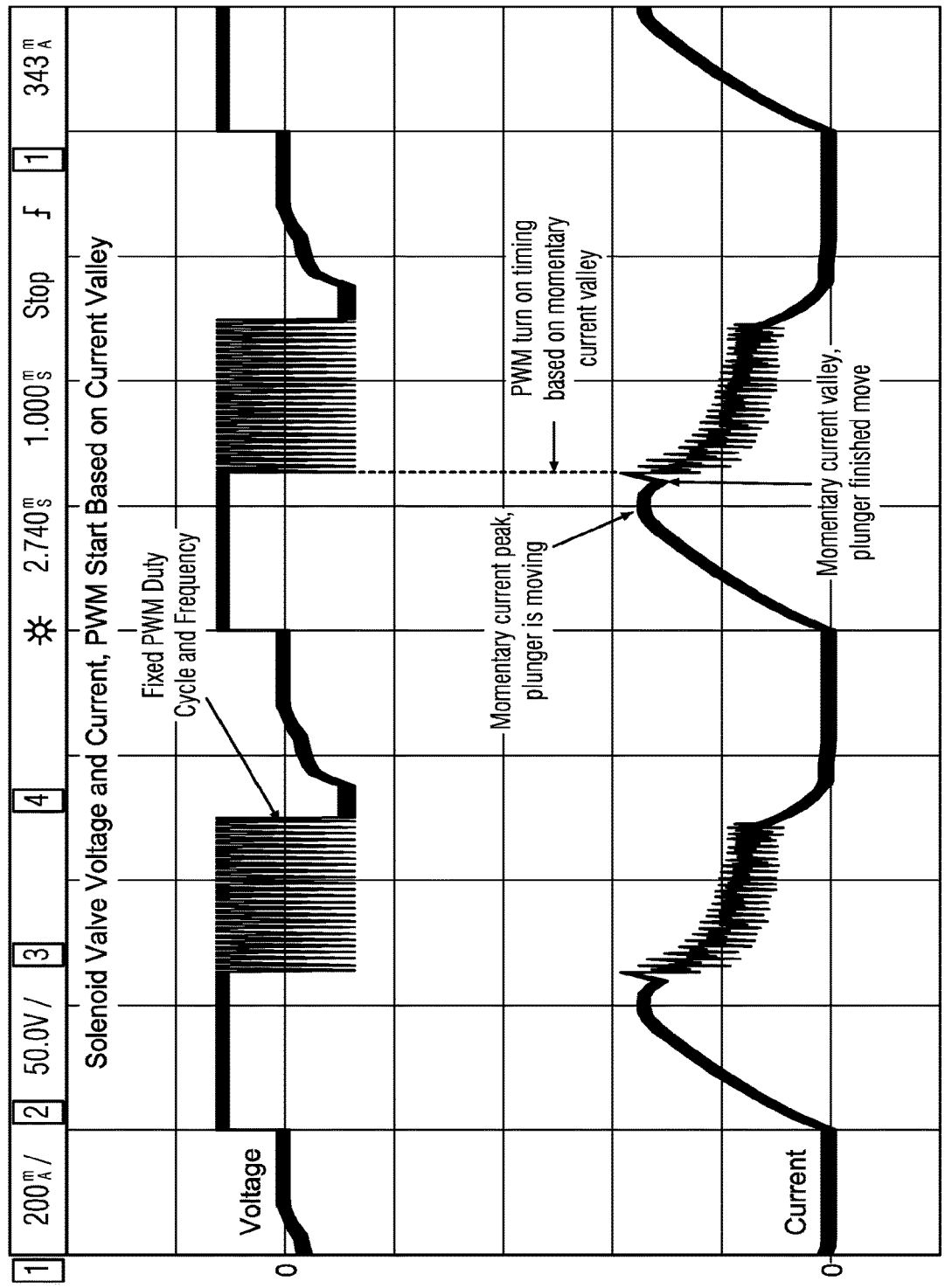
FIG. 6A illustrates an example of voltage and current over time of a solenoid vitrectomy drive valve and an optimization method using fixed pulse width modulation.

In some cases, the system control electronics and software can examine the current and determine that a solenoid plunger has moved based on a valley observed after the current signal initially falls due to back EMF and subsequently recovers. FIG. 6A illustrates an example of Voltage and Current over time of a solenoid vitrectomy drive valve and an optimization method using fixed pulse width modulation. The system control electronics and software can monitor the valve current in real time and detect a momentary current valley after the solenoid plunger finished moving. Based on detection of the valley, the system controller can initiate PWM with fixed duty cycle and fixed frequency. An initiation of PWM being triggered by the momentary current valley of an individual valve operating in specific conditions at a given valve cycle provides numerous benefits including the elimination of the delay for accommodating variations of the valve and its operation conditions. In this way it produces less heat in the solenoid vitrectomy drive valve which enhances reliability and prevents failure of the valve.

In some cases, the system control electronics and software accounts for noise in the current signal by requiring a threshold drop and rebound in current over a period of time before reporting a detected valley. For example, the system control electronics and software can sample the current and observe that the current is higher in each successive sample at a sampling rate (e.g. every ten microseconds). Next, the system control electronics and software can observe that a series of subsequent samples in a sampling band (e.g. the next ten sample over the next 100 microseconds) are successively lower and resulted in a total current drop greater than a predetermined threshold (e.g. 10 milliamps). Next, the system control electronics and software can observe that a series of subsequent samples in another sampling band (e.g. the next ten sample over the next 100 microseconds) are successively higher indicating a rebound. Next, the system control electronics and software can report a valley when the change in current drops greater than a predetermined threshold (e.g. 10 milliamps) followed by a rebound.

While specific examples of sampling rates, sampling bands, and threshold drops in current are listed as examples, those with ordinary skill in the art having the benefit of the present disclosure will readily appreciate that a wide variety of sampling rates, sampling bands, and threshold drops and rebounds in current can be utilized to achieve the benefits of the presently disclosed technology.

Figure 6B:
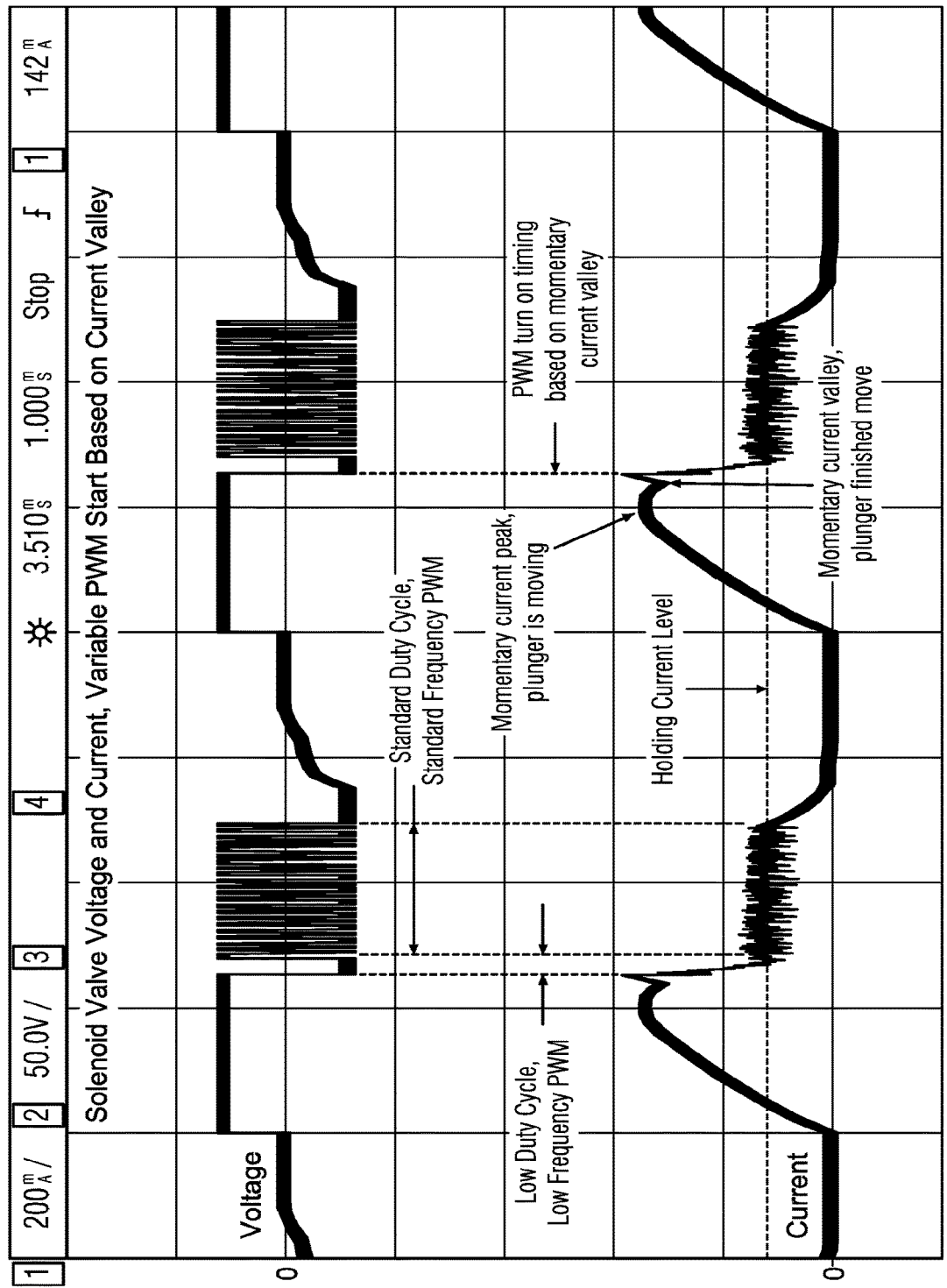
FIG. 6B illustrates an example of voltage and current over time of a solenoid vitrectomy drive valve and an optimization method using variable pulse width modulation.

The optimization example shown in FIG. 6A involves a PWM mode with a fixed duty cycle and a fixed frequency. In some cases, the system control electronics and software utilizes variable PWM duty cycle and frequency. With a variable PWM, the PWM starts with low duty cycle and low frequency to lower the current down to the holding current level very quickly and then changes the duty cycle and frequency to different values (standard duty cycle and standard frequency) to maintain the current at holding current level. Compared to fixed duty cycle and fixed frequency PWM, an optimization method using variable PWM can result in the solenoid vitrectomy drive valve producing less heat, which enhances reliability and prevents failure of the valve. FIG. 6B illustrates an example of Voltage and Current over time of a solenoid vitrectomy drive valve and an optimization method using variable pulse width modulation.

Figure 7:
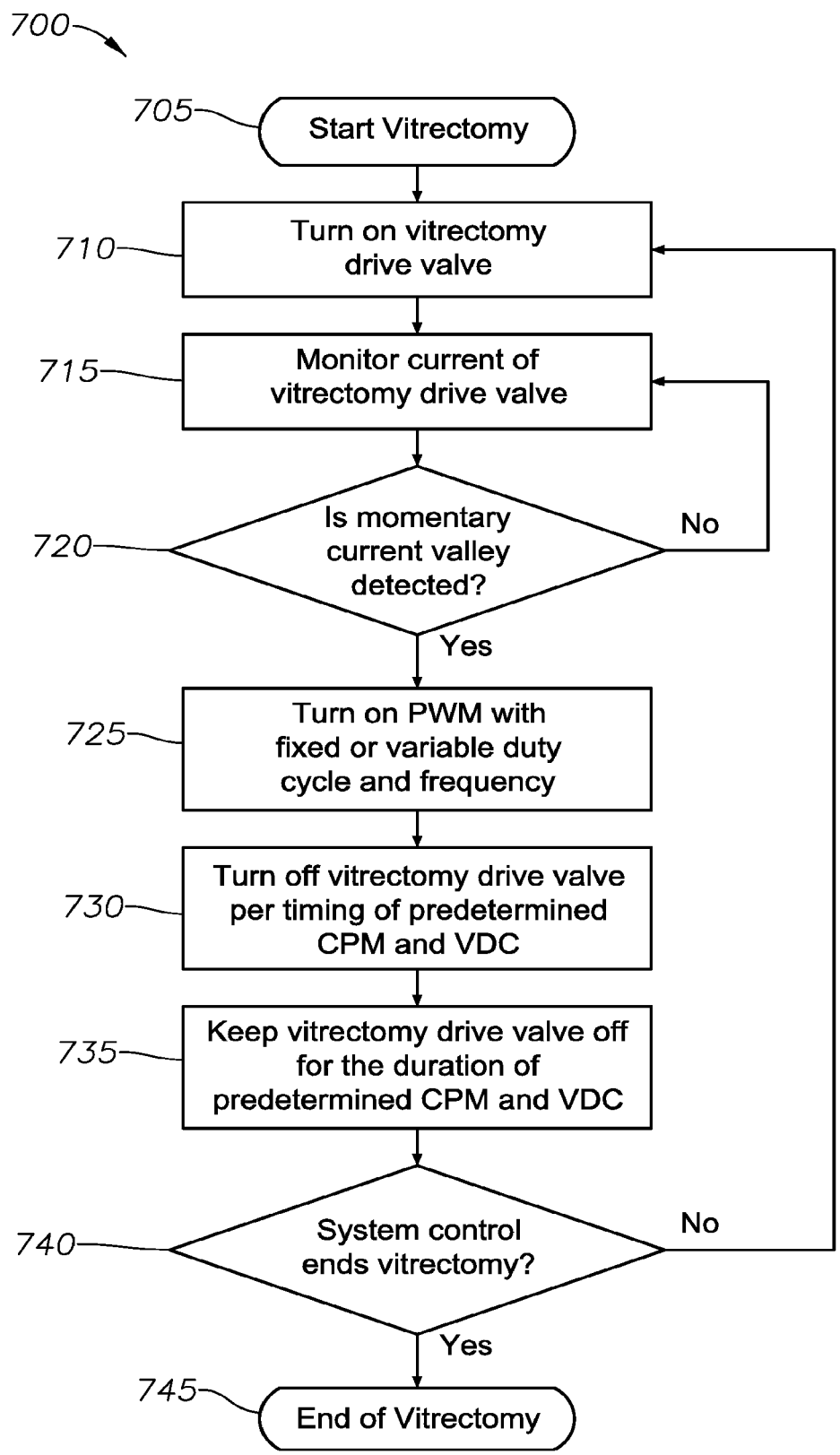
FIG. 7 illustrates a method of optimizing the application of pulse width modulation to the voltage applied to a pneumatic valve for driving a pneumatic chamber of a vitrectomy probe.

FIG. 7 illustrates a method 700 of optimizing the application of pulse width modulation to the voltage applied to a pneumatic valve for driving a pneumatic chamber of a vitrectomy probe. The method 700 involves initiating a vitrectomy procedure 705 that involves a solenoid controlled valve that controls pneumatic pressure being alternatively delivered to and vented from two chambers of a vitrectomy probe that separated by a diaphragm for driving the probe cutter. The method 700 involves turning on a vitrectomy drive valve 710 and monitoring the current of the vitrectomy drive valve 715, e.g. using a current sensor to monitor the current at a sample rate and reporting the current sample readings to a system controller.

Next, the method 700 involves determining whether a momentary current valley is detected 720, e.g. by the system controller processing the reported current sample readings, observing that the current is higher in each of a series of samples at the sampling rate, observing that a subsequent series of subsequent samples in a sampling band are successively lower and resulted in a total current drop greater than a predetermined threshold, observing that another series of subsequent samples are successively higher indicating a rebound in the current, momentary current valley is determined after the current rebounded from a valley indicating a movement of the solenoid plunger created back EMF.

When a valley is not detected, the method 700 involves continuing to monitor the current of the vitrectomy drive valve 715. Alternatively, when a valley is detected in the current, the method 700 involves turning on pulse width modulation (PWM) with a fixed or variable duty cycle and frequency 725. The application of PWM on the voltage delivered to the valve can continue until the end of the valve on cycle and the method 700 can next involve turning off the vitrectomy drive valve per the timing of the predetermined cut-per-minute (CPM) parameter and the valve duty cycle (VDC) 730. Next, the method 700 involves keeping the vitrectomy drive valve off for the duration of the predetermined CPM and VDC 735, e.g. to allow a first chamber to be vented and a second chamber to be driven with pressure.

Next, the method 700 involves determining when the system controller ends the vitrectomy 740. When the vitrectomy is not ended, the method 700 involves iterating by turning on the vitrectomy drive valve 710. When the vitrectomy ends, the method 700 involves ending the vitrectomy procedure 745.

Figure 8A:
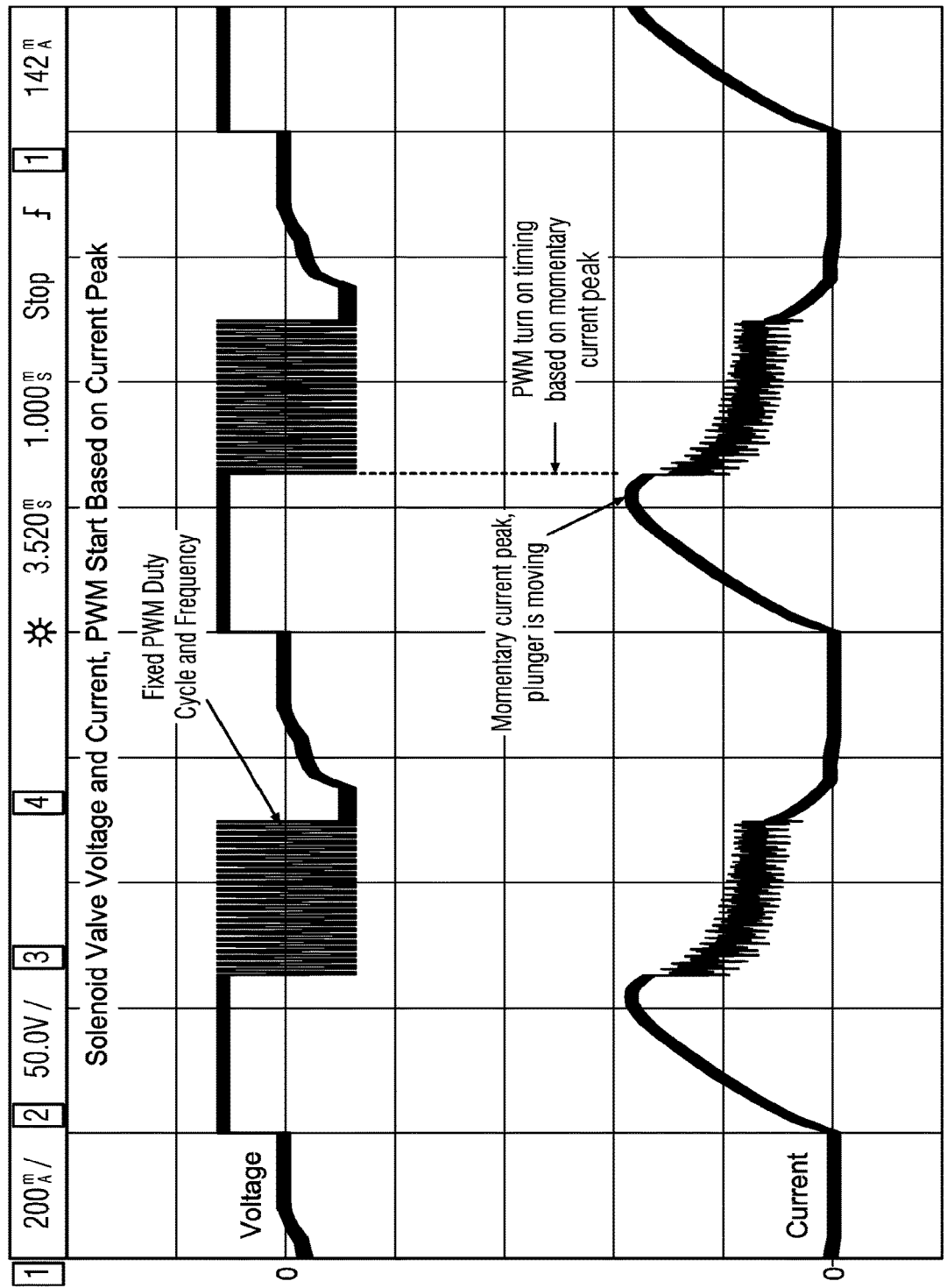
FIG. 8A illustrates an example of voltage and current over time of a solenoid vitrectomy drive valve and an optimization method using fixed pulse width modulation.

In some cases, the system control electronics and software can examine the current and determine that a solenoid plunger has moved based on a peak observed prior to a current falling due to back EMF. FIG. 8A illustrates an example of Voltage and Current over time of a solenoid vitrectomy drive valve and an optimization method using fixed pulse width modulation. The system control electronics and software can monitor the valve current in real time and detect a current peak. Based on detection of the peak, the system controller can initiate PWM with fixed duty cycle and fixed frequency. An initiation of PWM being triggered by the momentary current peak of an individual valve operating in specific conditions at a given valve cycle provides numerous benefits including the elimination of delay for accommodating variations of the valve and its operation conditions. This optimization reduces mechanical impact and noise of the solenoid valve because solenoid current is reduced substantially instantaneously after the solenoid plunger starts to move. In other words, the initiation of PWM upon detection of a peak reduces driving force before the solenoid plunger hits the hard stop. This optimization technique can also reduce more heat than an optimization technique based on valley detection since the PWM is initiated even earlier, which enhances reliability and prevents failure of the valve.

In some cases, the system control electronics and software accounts for noise in the current signal by requiring a threshold drop in current over a period of time before reporting the high point in current before the drop as a detected peak. For example, the system control electronics and software can sample the current and observe that the current is higher in each successive sample at a sampling rate (e.g. every ten microseconds). Next, the system control electronics and software can observe that a series of subsequent samples in a sampling band (e.g. the next ten sample over the next 100 microseconds) are successively lower and resulted in a total current drop greater than a predetermined threshold (e.g. 10 milliamps) and can report the high point of the current before the drop as a peak.

While specific examples of sampling rates, sampling bands, and threshold drops in current are listed as examples, those with ordinary skill in the art having the benefit of the present disclosure will readily appreciate that a wide variety of sampling rates, sampling bands, and threshold drops in current can be utilized to achieve the benefits of the presently disclosed technology.

Figure 8B:
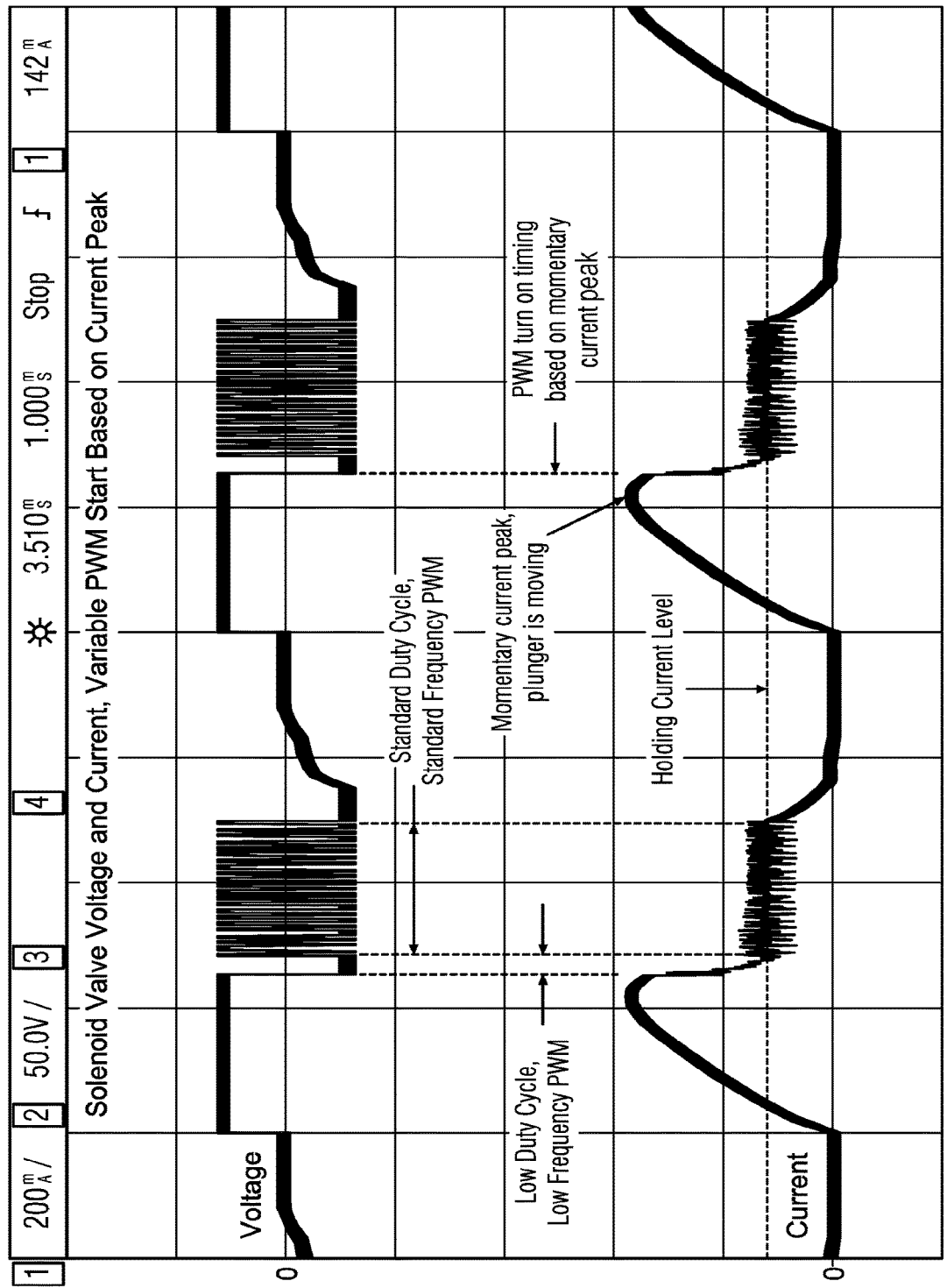
FIG. 8B illustrates an example of voltage and current over time of a solenoid vitrectomy drive valve and an optimization method using variable pulse width modulation.

The optimization example shown in FIG. 8A involves a PWM mode with a fixed duty cycle and a fixed frequency. In some cases, the system control electronics and software utilizes variable PWM duty cycle and frequency. With a variable PWM, the PWM based on fixed time delay, or detection of momentary current valley, or detection of momentary current peak, PWM starts with low duty cycle and low frequency to lower the current down to the holding current level very quickly and then changes the duty cycle and frequency to different values (standard duty cycle and standard frequency) to maintain the current at holding current level. Compared to fixed duty cycle and fixed frequency PWM, an optimization method using variable PWM can result in the solenoid vitrectomy drive valve producing less heat, which enhances reliability and prevents failure of the valve. FIG. 8B illustrates an example of Voltage and Current over time of a solenoid vitrectomy drive valve and an optimization method using variable pulse width modulation.

Figure 9:
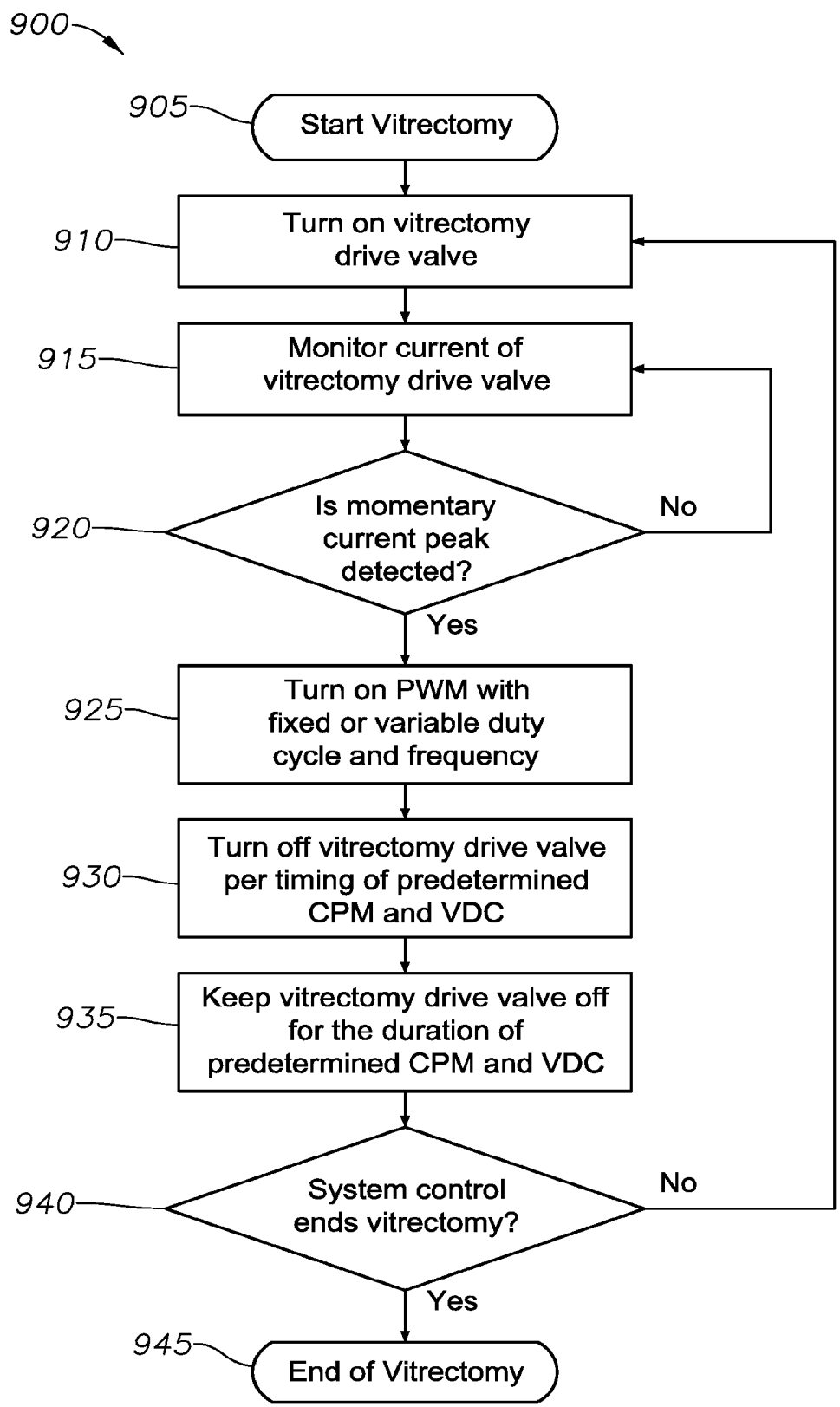
FIG. 9 illustrates a method of optimizing the application of pulse width modulation to the voltage applied to a pneumatic valve for driving a pneumatic chamber of a vitrectomy probe.

FIG. 9 illustrates a method 900 of optimizing the application of pulse width modulation to the voltage applied to a pneumatic valve for driving a pneumatic chamber of a vitrectomy probe. The method 900 involves initiating a vitrectomy procedure 905 that involves a solenoid controlled valve that controls pneumatic pressure being alternatively delivered to and vented from two chambers of a vitrectomy probe that separated by a diaphragm for driving the probe cutter. The method 900 involves turning on a vitrectomy drive valve 910 and monitoring the current of the vitrectomy drive valve 915, e.g. using a current sensor to monitor the current at a sample rate and reporting the current sample readings to a system controller.

Next, the method 900 involves determining whether a momentary current peak is detected 920, e.g. by the system controller processing the reported current sample readings, observing that the current is higher in each of a series of samples at the sampling rate, observing that a subsequent series of subsequent samples in a sampling band are successively lower and resulted in a total current drop greater than a predetermined threshold indicating a peak and a movement of the solenoid plunger created back EMF.

When a peak is not detected, the method 900 involves continuing to monitor the current of the vitrectomy drive valve 915. Alternatively, when a peak is detected in the current, the method 900 involves turning on pulse width modulation (PWM) with a fixed or variable duty cycle and frequency 925. The application of PWM on the voltage delivered to the valve can continue until the end of the valve on cycle and the method 900 can next involve turning off the vitrectomy drive valve per the timing of the predetermined cut-per-minute (CPM) parameter and the valve duty cycle (VDC) 930. Next, the method 900 involves keeping the vitrectomy drive valve off for the duration of the predetermined CPM and VDC 935, e.g. to allow a first chamber to be vented and a second chamber to be driven with pressure.

Next, the method 900 involves determining when the system controller ends the vitrectomy 940. When the vitrectomy is not ended, the method 900 involves iterating by turning on the vitrectomy drive valve 910. When the vitrectomy ends, the method 900 involves ending the vitrectomy procedure 945.

In some cases, a system controller, surgical console, or other computing device can collect and process the timing data of momentary current peaks and valleys. Based on the timing data, the system controller can adjust valve duty cycle to compensate variations in timing of valve open or close so that the desired pressure output can be reached for actuating the vitrectomy probe. Also based on the timing data falling in or out of a specific range, system controller can detect failures of the valve, track the performance or degradation of the valve, and advice for service of the valve.

Also, the system controller, surgical console, or other computing device can access a collection timing data and quantified instances of valve failure and train, using supervised learning, a machine learning algorithm to create a prediction model for predicting future valve failures based on real-time timing data of future valve operation. The failure prediction can be used to anticipate a failure prior to a subsequent vitrectomy procedure and allow an operator to replace the valve likely to fail.

Similarly, the system controller, surgical console, or other computing device can access a collection timing data and quantified instances of valve adjustments and outcomes and can train, using supervised learning, a machine learning algorithm to create an adjustment model to compensate variations in timing of valve open or close based on real-time timing data of a future valve operation.

Figure 10A:
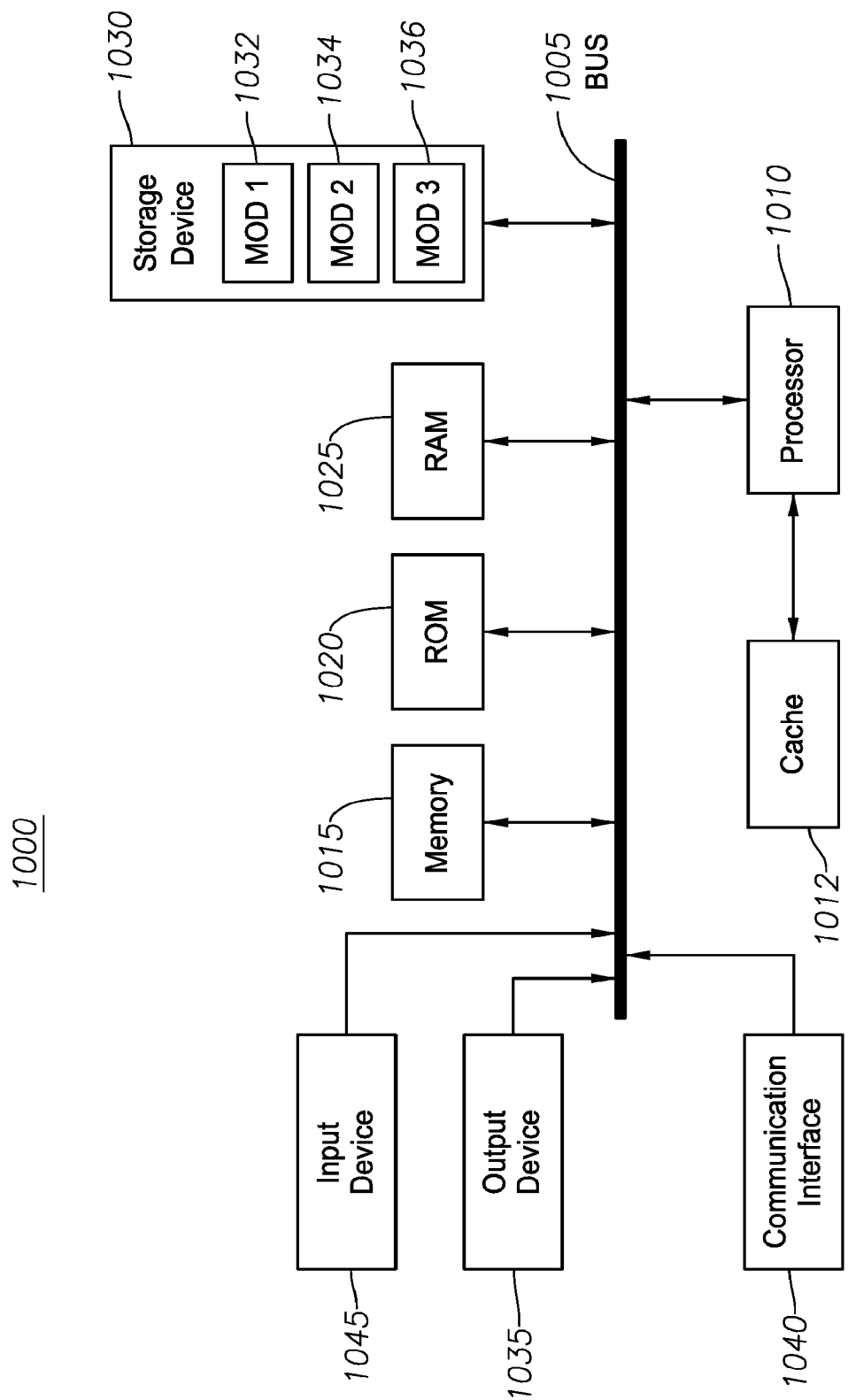
FIGS. 10A and 10B illustrate possible system embodiments.
Figure 10B:
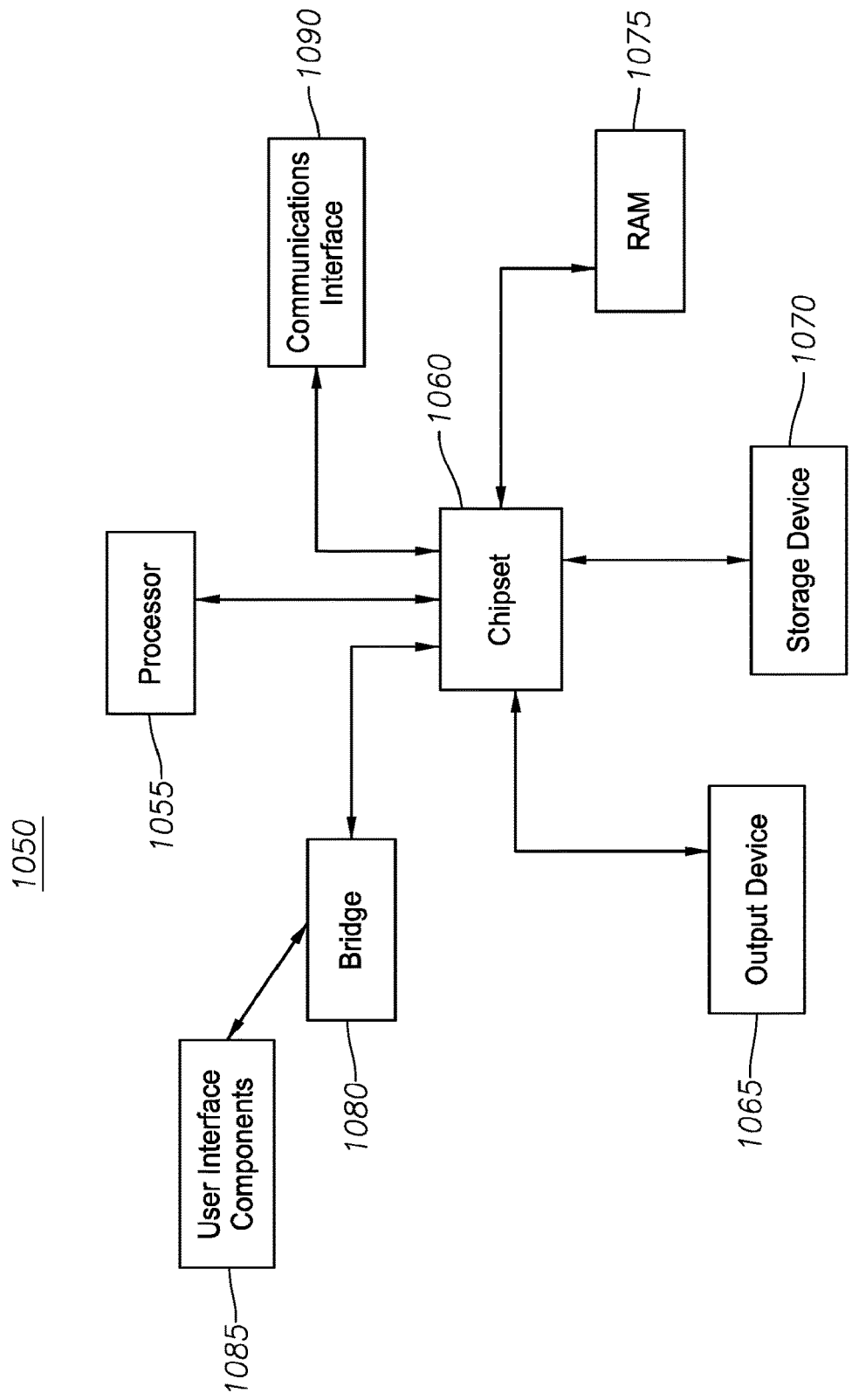

FIG. 10A and FIG. 10B illustrate possible system embodiments. The more appropriate embodiment will be apparent to those of ordinary skill in the art when practicing the present technology. Persons of ordinary skill in the art will also readily appreciate that other system embodiments are possible.

FIG. 10A illustrates a conventional system bus computing system architecture 1000 wherein the components of the system are in electrical communication with each other using a bus 1005. Exemplary system 1000 includes a processing unit (CPU or processor) 1010 and a system bus 1005 that couples various system components including the system memory 1015, such as read only memory (ROM) 1020 and random access memory (RAM) 1025, to the processor 1010. The system 1000 can include a cache of high-speed memory connected directly with, in close proximity to, or integrated as part of the processor 1010. The system 1000 can copy data from the memory 1015 and/or the storage device 1030 to the cache 1012 for quick access by the processor 1010. In this way, the cache can provide a performance boost that avoids processor 1010 delays while waiting for data. These and other modules can control or be configured to control the processor 1010 to perform various actions. Other system memory 1015 may be available for use as well. The memory 1015 can include multiple different types of memory with different performance characteristics. The processor 1010 can include any general purpose processor and a hardware module or software module, such as module 1 1032, module 2 1034, and module 3 1036 stored in storage device 1030, configured to control the processor 1010 as well as a special-purpose processor where software instructions are incorporated into the actual processor design. The processor 1010 may essentially be a completely self-contained computing system, containing multiple cores or processors, a bus, memory controller, cache, etc. A multi-core processor may be symmetric or asymmetric.

To enable user interaction with the computing device 1000, an input device 1045 can represent any number of input mechanisms, such as a microphone for speech, a touch-sensitive screen for gesture or graphical input, keyboard, mouse, motion input, speech and so forth. An output device 1035 can also be one or more of a number of output mechanisms known to those of skill in the art. In some instances, multimodal systems can enable a user to provide multiple types of input to communicate with the computing device 1000. The communications interface 1040 can generally govern and manage the user input and system output. There is no restriction on operating on any particular hardware arrangement and therefore the basic features here may easily be substituted for improved hardware or firmware arrangements as they are developed.

Storage device 1030 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1025, read only memory (ROM) 1000, and hybrids thereof.

The storage device 1030 can include software modules 1032, 1034, 1036 for controlling the processor 1010. Other hardware or software modules are contemplated. The storage device 1030 can be connected to the system bus 1005. In one aspect, a hardware module that performs a particular function can include the software component stored in a computer-readable medium in connection with the necessary hardware components, such as the processor 1010, bus 1005, display 1035, and so forth, to carry out the function.

FIG. 10B illustrates a computer system 1050 having a chipset architecture that can be used in executing the described method and generating and displaying a graphical user interface (GUI). Computer system 1050 is an example of computer hardware, software, and firmware that can be used to implement the disclosed technology. System 1050 can include a processor 1055, representative of any number of physically and/or logically distinct resources capable of executing software, firmware, and hardware configured to perform identified computations. Processor 1055 can communicate with a chipset 1060 that can control input to and output from processor 1055. In this example, chipset 1060 outputs information to output 1065, such as a display, and can read and write information to storage device 1070, which can include magnetic media, and solid state media, for example. Chipset 1060 can also read data from and write data to RAM 1075. A bridge 1080 for interfacing with a variety of user interface components 1085 can be provided for interfacing with chipset 1060. Such user interface components 1085 can include a keyboard, a microphone, touch detection and processing circuitry, a pointing device, such as a mouse, and so on. In general, inputs to system 1050 can come from any of a variety of sources, machine generated and/or human generated.

Chipset 1060 can also interface with one or more communication interfaces 1090 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 1055 analyzing data stored in storage 1070 or 1075. Further, the machine can receive inputs from a user via user interface components 1085 and execute appropriate functions, such as browsing functions by interpreting these inputs using processor 1055.

It can be appreciated that exemplary systems 1000 and 1050 can have more than one processor 1010, or 1055, or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data that cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, Universal Serial Bus (USB) devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method of optimizing control of a solenoid valve for operating a vitrectomy probe comprising:
   coupling a valve with a pressurized gas source, a power supply for supplying a voltage to drive a current in a solenoid in the valve, and a vitrectomy probe with a first chamber and a second chamber on respective sides of a pneumatically driven diaphragm for reciprocating a probe cutter;
   delivering, by the power supply, the voltage to supply the solenoid with the current which drives a solenoid plunger to alternatively deliver and vent pressurized gas through a first outlet line and a second outlet line which respectively deliver and vent the pressurized gas to and from the first chamber and to and from the second chamber of the vitrectomy probe;
   monitoring, with a current sensor coupled to the solenoid, the current in the solenoid;
   transmitting, by the current sensor to a system controller, a current signal;
   receiving, by the system controller, the current signal from the current sensor;
   identifying, by the system controller, when a plunger movement in the solenoid creates a back electromotive force (back EMF) that changes the current in the solenoid in a predetermined degree, wherein identifying when the plunger movement in the solenoid creates the back EMF further comprises the system controller:
   observing that the current is higher in each of a series of samples at a sampling rate;
   observing that a subsequent series of subsequent samples in a sampling band are successively lower and resulted in a total current drop greater than a predetermined threshold indicating a peak;
   observing that another series of subsequent samples are successively higher indicating a rebound in the current after the current rebounded from a valley; and
   identifying a movement of the solenoid plunger created back EMF by observing the peak and valley;
   causing, by the system controller, the power supply to enter a pulse width modulation (PWM) mode of operation to cause a continued movement of the solenoid plunger and/or hold an end position of the solenoid plunger until power to the solenoid is turned off at a predetermined timing after detecting the back EMF;
   collecting current data associated with the detected peaks and valleys of the current signal;
   predicting, via a failure prediction model, a future valve failure, wherein the failure prediction model is trained based on quantified instances of valve failure determined from the collected current data; and
   displaying, on a surgical console coupled to the vitrectomy probe, advice for service of the valve based on the predicted future valve failure.

2. The method of claim 1, wherein the quantified instances of valve failure are detected through the current data falling in or out of a specified range.

3. The method of claim 1, further comprising tracking performance of the valve based on the current data falling in or out of a specified range.

4. The method of claim 1, further comprising tracking degradation of the valve based on the current data falling in or out of a specified range.

5. The method of claim 1, further comprising training, via supervised learning, the failure prediction model for predicting future valve failures based on real-time current data of a future valve operation.

6. The method of claim 1, further comprising based on the collected current data, adjusting valve duty cycle of the valve to compensate for variations in timing of valve open or close so that a desired pressure output can be reached for actuating the vitrectomy probe.

7. The method of claim 1, wherein displaying advice for service of the valve based on the predicted future valve failure occurs prior to a subsequent vitrectomy procedure using the surgical console.

8. The method of claim 1, wherein the predetermined threshold is 10 milliamps.

9. The method of claim 1, wherein the PWM mode comprises a constant PWM with a fixed duty cycle and a fixed frequency.

10. The method of claim 1, wherein the PWM mode comprises a variable PWM with a variable duty cycle and a variable frequency.

11. The method of claim 1, wherein the collected current data comprises timing data describing a timing associated with the detected peaks and valleys of the current signal.

* * * * *